US012806373B2

(12) United States Patent
Rhodes et al.

(10) Patent No.: US 12,806,373 B2
(45) Date of Patent: Nov. 24, 2026

(54) COUPLER FOR ORGANIZING AND RELEASABLY CLAMPING CATHETER COMPONENTS AND METHODS OF USE

(71) Applicant: Route 92 Medical, Inc., San Mateo, CA (US)

(72) Inventors: David Rhodes, San Mateo, CA (US); Tony M. Chou, San Mateo, CA (US); John Miller, San Mateo, CA (US)

(73) Assignee: Route 92 Medical, Inc., West Jordan, UT (US)

( * ) Notice: Subject to any disclaimer, the term of this patent is extended or adjusted under 35 U.S.C. 154(b) by 756 days.

(21) Appl. No.: 18/184,495

(22) Filed: Mar. 15, 2023

(65) Prior Publication Data

US 2023/0293851 A1 Sep. 21, 2023

Related U.S. Application Data

(60) Provisional application No. 63/425,236, filed on Nov. 14, 2022, provisional application No. 63/320,615, filed on Mar. 16, 2022.

(51) Int. Cl.
*A61M 25/01* (2006.01)
*A61M 25/09* (2006.01)

(52) U.S. Cl.
CPC ... *A61M 25/01* (2013.01); *A61M 2025/09116* (2013.01); *A61M 2025/09125* (2013.01)

(58) Field of Classification Search
CPC .... A61M 25/01; A61M 25/02; A61M 25/013; A61M 2025/09116; A61M 2025/09125; A61M 2025/0006; A61M 2025/024
See application file for complete search history.

(56) References Cited

U.S. PATENT DOCUMENTS 3,696,920 A 10/1972 Lahay
4,687,470 A * 8/1987 Okada .................. A61M 25/02 604/270
4,784,647 A 11/1988 Gross
4,801,294 A * 1/1989 Okada .................. A61M 25/02 604/161

(Continued)

OTHER PUBLICATIONS

U.S. Appl. No. 16/584,351, filed Sep. 26, 2019, US 2020-0038628.

(Continued)

*Primary Examiner* — William H Rodriguez
(74) *Attorney, Agent, or Firm* — Mintz Levin Cohn Ferris Glovsky and Popeo, P.C.

(57) ABSTRACT

An intravascular access system for facilitation of intraluminal medical procedures within a vasculature including an outer catheter having a tubular distal portion having a lumen and a proximal extension without a lumen; an inner catheter having a flexible elongate body; and at least one coupler configured to be affixed to at least a portion of the proximal extension and at least a portion of the flexible elongate body to accommodate different relative positions between the outer catheter and the inner catheter during movement of the inner and outer catheters through the vasculature. The at least one coupler has a unitary elastic body with at least one slot configured to receive and retain the proximal extension and the flexible elongate body. Related devices, systems, and methods are provided.

16 Claims, 10 Drawing Sheets

(56) References Cited

U.S. PATENT DOCUMENTS

| | | | | |
|---|---|---|---|---|
| 4,829,999 | A * | 5/1989 | Auth | A61M 25/09041 606/1 |
| 4,946,443 | A | 8/1990 | Hauser et al. | |
| 4,971,271 | A | 11/1990 | Sularz | |
| 5,046,624 | A | 9/1991 | Murphy et al. | |
| 5,364,355 | A * | 11/1994 | Alden | A61M 25/00 604/103.09 |
| 5,380,276 | A * | 1/1995 | Miller | A61M 25/0032 604/28 |
| 5,527,292 | A | 6/1996 | Adams et al. | |
| D378,408 | S | 3/1997 | Pyeatt et al. | |
| 5,967,988 | A * | 10/1999 | Briscoe | A61M 25/01 600/458 |
| 6,213,988 | B1 * | 4/2001 | McIvor | A61M 25/01 604/165.01 |
| 6,544,251 | B1 * | 4/2003 | Crawford | A61M 25/02 604/537 |
| D478,738 | S | 8/2003 | Workman | |
| 7,220,246 | B2 | 5/2007 | Raulerson et al. | |
| D563,551 | S | 3/2008 | Schweikert et al. | |
| D567,372 | S | 4/2008 | Chesnin | |
| D568,723 | S | 5/2008 | Morgan | |
| D568,991 | S | 5/2008 | Schweikert et al. | |
| D569,972 | S | 5/2008 | Schweikert | |
| D571,005 | S | 6/2008 | Chesnin et al. | |
| 7,413,561 | B2 | 8/2008 | Raulerson et al. | |
| D592,303 | S | 5/2009 | Chesnin | |
| 7,604,612 | B2 | 10/2009 | Ressemann et al. | |
| 7,736,355 | B2 | 6/2010 | Itou et al. | |
| D622,839 | S | 8/2010 | Fisher et al. | |
| 7,827,656 | B2 | 11/2010 | Schweikert | |
| D638,690 | S | 5/2011 | Hoek | |
| D638,691 | S | 5/2011 | Hoek | |
| D638,692 | S | 5/2011 | Hoek | |
| D639,145 | S | 6/2011 | Hoek | |
| D640,527 | S | 6/2011 | Hoek | |
| D644,501 | S | 9/2011 | Chen | |
| 8,048,032 | B2 | 11/2011 | Root et al. | |
| D657,460 | S | 4/2012 | Uhlenkamp et al. | |
| D657,869 | S | 4/2012 | Mammen | |
| 8,246,585 | B2 | 8/2012 | Schennib | |
| 8,267,370 | B2 | 9/2012 | Fisher et al. | |
| 8,613,728 | B2 | 12/2013 | Amisar et al. | |
| D701,303 | S | 3/2014 | Cook | |
| 8,996,095 | B2 | 3/2015 | Anderson et al. | |
| 8,998,151 | B2 | 4/2015 | Hoek | |
| D734,485 | S | 7/2015 | Oonuma et al. | |
| D749,209 | S | 2/2016 | Uhlenkamp et al. | |
| D782,024 | S | 3/2017 | Murphy | |
| 9,820,761 | B2 | 11/2017 | Garrison et al. | |
| 10,124,146 | B2 | 11/2018 | Di Caprio et al. | |
| 10,183,146 | B2 | 1/2019 | Yang et al. | |
| 10,192,230 | B2 | 1/2019 | Look et al. | |
| D852,354 | S | 6/2019 | Wrangmark et al. | |
| D907,988 | S | 1/2021 | Yu | |
| D909,188 | S | 2/2021 | Kou | |
| 11,065,019 | B1 * | 7/2021 | Chou | A61B 17/221 |
| D928,311 | S | 8/2021 | McVaney | |
| 11,224,450 | B2 | 1/2022 | Chou et al. | |
| 11,400,255 | B1 | 8/2022 | Chou et al. | |
| 11,491,313 | B2 | 11/2022 | Fischell et al. | |
| D981,825 | S | 3/2023 | Hu | |
| D996,609 | S | 8/2023 | Gandee et al. | |
| 11,806,032 | B2 * | 11/2023 | Chou | A61M 25/0068 |
| 11,941,313 | B2 | 3/2024 | Kumakura et al. | |
| 12,521,521 | B2 * | 1/2026 | Chou | A61M 25/0026 |
| 2003/0188403 | A1 | 10/2003 | Lemke et al. | |
| 2003/0195546 | A1 | 10/2003 | Solar et al. | |
| 2005/0038453 | A1 | 2/2005 | Raulerson | |
| 2005/0277909 | A1 * | 12/2005 | McDaniel | A61M 25/02 604/523 |
| 2007/0010863 | A1 | 1/2007 | Stenzel | |
| 2008/0092349 | A1 | 4/2008 | Cofer | |
| 2009/0143740 | A1 * | 6/2009 | Bierman | A61M 5/1415 604/177 |
| 2009/0264865 | A1 | 10/2009 | Kawai | |
| 2013/0035628 | A1 | 2/2013 | Garrison et al. | |
| 2013/0274783 | A1 | 10/2013 | Wynberg | |
| 2013/0281788 | A1 | 10/2013 | Garrison | |
| 2015/0173782 | A1 | 6/2015 | Garrison et al. | |
| 2016/0074628 | A1 | 3/2016 | Smith et al. | |
| 2017/0020540 | A1 * | 1/2017 | Chou | A61B 17/22 |
| 2017/0143938 | A1 | 5/2017 | Ogle et al. | |
| 2017/0224953 | A1 | 8/2017 | Tran et al. | |
| 2018/0193042 | A1 * | 7/2018 | Wilson | A61B 17/22 |
| 2018/0207399 | A1 * | 7/2018 | Chou | A61M 25/09 |
| 2018/0242978 | A1 | 8/2018 | Chou et al. | |
| 2018/0339130 | A1 | 11/2018 | Ogle | |
| 2018/0361114 | A1 * | 12/2018 | Chou | A61B 17/1204 |
| 2019/0183517 | A1 | 6/2019 | Ogle | |
| 2019/0351182 | A1 * | 11/2019 | Chou | A61B 17/22 |
| 2020/0289136 | A1 * | 9/2020 | Chou | A61B 17/22 |
| 2021/0212707 | A1 * | 7/2021 | Chou | A61B 17/22 |
| 2021/0228844 | A1 | 7/2021 | Ogle | |
| 2021/0330332 | A1 | 10/2021 | Chou et al. | |
| 2022/0111177 | A1 * | 4/2022 | Chou | A61B 17/12109 |
| 2022/0161002 | A1 | 5/2022 | Wang et al. | |
| 2023/0029243 | A1 | 1/2023 | Ogle | |
| 2023/0042898 | A1 * | 2/2023 | Howell | A61M 25/0606 |
| 2023/0248377 | A1 | 8/2023 | Wainwright et al. | |
| 2023/0293851 | A1 | 9/2023 | Rhodes et al. | |
| 2023/0355255 | A1 * | 11/2023 | Chou | A61F 2/966 |
| 2023/0355413 | A1 | 11/2023 | Garrison et al. | |
| 2023/0380915 | A1 * | 11/2023 | Hundertmark | A61B 34/30 |
| 2024/0016633 | A1 * | 1/2024 | Garrison | A61F 2/962 |
| 2024/0164801 | A1 | 5/2024 | Wainwright et al. | |
| 2024/0198039 | A1 | 6/2024 | Wainwright et al. | |

OTHER PUBLICATIONS

U.S. Appl. No. 16/890,962, filed Jun. 2, 2020, US 2020/0289136.

U.S. Appl. No. 17/011,448, filed Sep. 3, 2020, US 2021-0052296.

U.S. Appl. No. 17/089,495, filed Nov. 4, 2020, US 2021-0045758.

U.S. Appl. No. 17/093,401, filed Nov. 9, 2020, US 2021-0069467.

U.S. Appl. No. 17/319,943, filed May 13, 2021, US 2021-0259718.

U.S. Appl. No. 17/497,713, filed Oct. 8, 2021, US 2022-0111177.

U.S. Appl. No. 17/545,885, filed Dec. 8, 2021, US 2022-0096103.

U.S. Appl. No. 17/849,379, filed Jun. 24, 2022, US 2022-0313292.

U.S. Appl. No. 17/859,955, filed Jul. 7, 2022, US 2022-0338888.

U.S. Appl. No. 17/883,295, filed Aug. 8, 2022, US 2022-0370767.

U.S. Appl. No. 17/981,164, filed Nov. 4, 2022, US 2023-0059721.

U.S. Appl. No. 18/065,527, filed Dec. 13, 2022, US 2023-0248366.

U.S. Appl. No. 18/159,491, filed Jan. 25, 2023, US 2023-0165597.

U.S. Appl. No. 18/185,710, filed Mar. 17, 2023, US 2023-0277805.

U.S. Appl. No. 18/297,443, filed Apr. 7, 2023, US 2023-0241348.

U.S. Appl. No. 18/297,450, filed Apr. 7, 2023, US 2023-0263995.

U.S. Appl. No. 18/309,173, filed Apr. 28, 2023, US 2023-0277806.

U.S. Appl. No. 18/311,797, filed May 3, 2023, US 2023-0355255.

U.S. Appl. No. 18/311,802, filed May 3, 2023, US 2023-0355413.

U.S. Appl. No. 18/323,756, filed May 25, 2023, US 2023-0380915.

U.S. Appl. No. 18/350,533, filed Jul. 11, 2023, US 2024-0016633.

U.S. Appl. No. 18/369,695, filed Sep. 18, 2023, US 2024-0009425.

U.S. Appl. No. 18/485,168, filed Oct. 11, 2023, US 2024-0042170.

U.S. Appl. No. 18/514,553, filed Nov. 20, 2023, US 2024-0082542.

PCT/US2023/20868, May 3, 2023, WO 2023/215402.

PCT/US2023/20871, May 3, 2023, WO 2023/215403.

PCT/US2023/23574, May 3, 2023, WO 2023/230259.

PCT/US2023/27404, Jul. 11, 2023, WO 2024/015382.

PCT/US2023/64454, Mar. 15, 2023, WO 2023/178189.

* cited by examiner

COUPLER FOR ORGANIZING AND RELEASABLY CLAMPING CATHETER COMPONENTS AND METHODS OF USE

CROSS-REFERENCE TO RELATED APPLICATIONS

The present application claims priority to U.S. Provisional Application No. 63/425,236, filed Nov. 14, 2022, and entitled, "Coupler for Organizing and Releasably Clamping Catheter Components and Methods of Use," and U.S. Provisional Application No. 63/320,615, filed Mar. 16, 2022, and entitled, "Coupler for Organizing and Releasably Clamping Catheter Components and Methods of Use," the entirety of each of which is incorporated by reference herein.

FIELD

The present technology relates generally to medical devices and methods, and more particularly, to couplers for organizing and releasably clamping catheter components and their methods of use.

BACKGROUND

To access the vascular anatomy, guide catheters or guide sheaths are used to guide interventional devices to the target anatomy from an access site, such as the femoral artery. The length of the guide is determined by the distance between the access site and the desired location of the guide distal tip. Interventional devices such as guidewires, microcatheters, and intermediate catheters used for sub-selective guides and aspiration, are inserted through the guide and advanced to the target site. Often, devices are used in a co-axial fashion, namely, a guidewire inside a microcatheter inside an intermediate catheter is advanced as an assembly to the vascular target site in a stepwise fashion with the innermost atraumatic elements, advancing distally first and providing support for advancement of the outer elements. Some systems of intravascular access devices enable "monopoint" access. These systems are single-operator systems that allow the operator to work at a single proximal hub and, in the case of catheters having proximal rail segment that are not full-length catheters, can manipulate all the elements being used to navigate the intravascular anatomy with single-handed "pinches." These pinches, however, can lead to inadvertent slippage between the components. Slippage can cause a user's desired assembled configuration for the components to be lost as they are advanced through tortuous anatomy leading to difficulties in navigation and procedural delays. Delays and difficulties in vascular navigation, especially for the treatment of acute stroke, can be particularly detrimental to a patient's health.

SUMMARY

Systems, methods, and articles of manufacture are provided for a coupler for organizing and releasably clamping catheter components.

According to some interrelated aspects, an intravascular access system for facilitation of intraluminal medical procedures within a vasculature includes an outer catheter, an inner catheter and at least one coupler. The outer catheter includes a tubular distal portion having a lumen and a proximal extension without a lumen. The inner catheter includes a flexible elongate body. The at least one coupler is configured to be affixed to at least a portion of the proximal extension and at least a portion of the flexible elongate body to accommodate different relative positions between the outer catheter and the inner catheter during movement of the inner catheter and the outer catheter through the vasculature. The at least one coupler includes a unitary elastic body with at least one slot configured to receive and retain the proximal extension and the flexible elongate body.

In some aspects, the at least one coupler further includes a pair of wings configured to be manipulated to open the coupler.

In some aspects, the at least one coupler is V-shaped and the pair of wings are movable relative to one another to widen the at least one slot.

In some aspects, the system includes at least two couplers.

In some aspects, the coupler and at least one of the inner catheter and the outer catheter is packaged together in a sterile package.

In some aspects, the coupler includes a spring configured to increase a grip force for manipulating the pair of wings.

In some aspects, the spring is positioned between the pair of wings.

In some aspects, the at least one slot is positioned on a side of the coupler, and the pair of wings are positioned on the side.

In some aspects, the at least one slot is positioned on a first side of the coupler, and the pair of wings are positioned on a second side opposite the first side.

In some aspects, manipulation of the pair of wings towards one another is configured to cause the at least one slot to unlock, thereby allowing the proximal extension and/or the flexible elongate body to be positioned within the at least one slot or removed from the at least one slot.

In some aspects, manipulation of the pair of wings away from one another is configured to cause the at least one slot to unlock, thereby allowing the proximal extension and/or the flexible elongate body to be positioned within the at least one slot or removed from the at least one slot.

In some aspects, release of the pair of wings is configured to cause the at least one slot to lock, thereby preventing movement of the proximal extension and/or the flexible elongate body relative to one another.

In some aspects, the at least one slot defines a clamp configured to secure at least one of the proximal extension and the flexible elongate body.

In some aspects, the clamp includes a first clamp portion and a second clamp portion positioned parallel to the first clamp portion.

In some aspects, the clamp includes a first clamp insert and a second clamp insert configured to engage at least one of the proximal extension and the flexible elongate body. The first clamp insert and the second clamp insert include one or more of a foam and an elastomer.

In some aspects, the clamp includes a hinge configured to allow the first clamp portion and the second clamp portion to be rotated away from one another.

In some aspects, the at least one coupler is removable such that the at least one coupler is configured to be removably affixed to at least the portion of the proximal extension and at least the portion of the flexible elongate body.

In some aspects, the at least one coupler is integrally formed with one of the proximal extension and the flexible elongate body.

In some aspects, the at least one coupler comprises a coupling feature configured to receive the other one of the proximal extension and the flexible elongate body.

In some aspects, the coupling features includes the at least one slot.

In some aspects, the at least one coupler is slidable along at least one of the proximal extension and the flexible elongate body.

In some aspects, the at least one coupler includes an identifier indicating at least one of the proximal extension and the flexible elongate body coupled to the at least one coupler.

According to some interrelated aspects, a catheter system for facilitation of medical procedures within a vasculature includes a first medical device having a proximal end, a distal end and a lumen, a second medical device having a proximal end and a distal end and configured to be at least partially inserted into the lumen of the first medical device, and at least one removable coupler configured to be removably affixed to at least a portion of the proximal ends of both the first and second medical devices to axially fix the first and second medical devices together during movement of the catheter system in the vasculature. The at least one removable coupler includes a unitary elastic body with at least one slot configured to receive and retain the proximal ends of the first and second medical devices.

In some interrelated aspects, a method of performing a medical procedure within a vasculature includes providing a first medical device having a proximal end portion without a lumen and a distal end portion with a lumen. The method also includes inserting a second medical device having a proximal end and a distal end into the lumen of the first medical device. The method also includes providing a removable coupler comprising a unitary elastic body with at least one slot configured to receive and retain the proximal ends of the first and second medical devices. The method also includes attaching the removable coupler to at least a portion of the proximal ends of both the first and second medical devices to axially fix the first and second medical devices with respect to one another. The method also includes moving the first and second medical devices within together within the vasculature.

In some aspects, the first medical device proximal end comprises a wire or ribbon.

In some aspects, the second medical device includes a delivery catheter having a tapered tip and a single lumen. In some aspects, the second medical device includes an aspiration catheter with a single lumen and a proximal rotating hemostasis valve.

In some aspects, the removable coupler is manually actuated to open the slot and allow the first and second medical devices to be removed from the coupler.

In some aspects, the removable coupler is attached to the first and second medical devices to axially fix the first and second medical devices with respect to one another outside of a patient's body, the first and second medical devices are advanced together through the patient's vasculature, and the removable coupler is detached from at least one of the first or second medical devices to allow at least one of the first and second medical devices to be removed from the patient's body independently.

In some aspects, the removable coupler remains outside of the patient's body during the medical procedure.

In some aspects, the method also includes providing a third medical device. The removable coupler is attached to at least a portion of a proximal end of the third medical device.

In some aspects, the removable coupler further includes a pair of wings configured to be manipulated to open the removable coupler. The removable coupler is removed from the first and second medical device by manual actuation of the wings.

According to some interrelated aspects, a coupler is provided for an intravascular access system for facilitation of intraluminal medical procedures within a vasculature. The coupler includes a unitary elastic body, a slot configured to receive and retain at least two medical devices, and a pair of wings configured to be manipulated to open the coupler. The coupler is configured to be affixed to at least a portion of the at least two medical devices to accommodate different relative positions between the at least two medical devices during movement of the at least two medical devices through the vasculature.

In some aspects, the at least two medical devices includes: an outer catheter comprising a tubular distal portion having a lumen and a proximal extension without a lumen, and an inner catheter having a flexible elongate body.

In some aspects, the coupler is V-shaped and the pair of wings are movable relative to one another to widen the slot.

In some aspects, the coupler includes a spring configured to increase a grip force for manipulating the pair of wings.

In some aspects, the spring is positioned between the pair of wings.

In some aspects, the slot is positioned on a side of the coupler, and the pair of wings are positioned on the side.

In some aspects, the slot is positioned on a first side of the coupler, and the pair of wings are positioned on a second side opposite the first side.

In some aspects, manipulation of the pair of wings towards one another is configured to cause the at least one slot to unlock, thereby allowing the at least two medical devices to be positioned within the slot or removed from the slot.

In some aspects, manipulation of the pair of wings away from one another is configured to cause the at least one slot to unlock, thereby allowing the at least two medical devices to be positioned within the slot or removed from the slot.

In some aspects, release of the pair of wings is configured to cause the slot to lock, thereby preventing movement of the at least two medical devices relative to one another.

In some aspects, the slot defines a clamp configured to secure at least one of the at least two medical devices. In some aspects, the clamp includes a first clamp portion and a second clamp portion positioned parallel to the first clamp portion. In some aspects, the clamp includes a first clamp insert and a second clamp insert configured to engage at least one of the at least two medical devices. The first clamp insert and the second clamp insert can include one or more of a foam and an elastomer. In some aspects, the clamp includes a hinge configured to allow the first clamp portion and the second clamp portion to be rotated away from one another.

In some aspects, the at least one coupler is removable such that the at least one coupler is configured to be removably affixed to at least the portion of the at least two medical devices.

In some aspects, the at least one coupler is integrally formed with one of the at least two medical devices.

In some aspects, the coupler includes a coupling feature configured to receive another one of the at least two medical devices. In some aspects, the coupling features includes the slot.

In some aspects, the coupler is slidable along at least one of the at least two medical devices.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes, it should be readily understood that such features are not intended to be limiting. The claims that follow this disclosure are intended to define the scope of the protected subject matter.

BRIEF DESCRIPTION OF THE DRAWINGS

These and other aspects will now be described in detail with reference to the following drawings. Generally speaking the figures are not to scale in absolute terms or comparatively, but are intended to be illustrative. Also, relative placement of features and elements may be modified for the purpose of illustrative clarity.

Figure 1A:
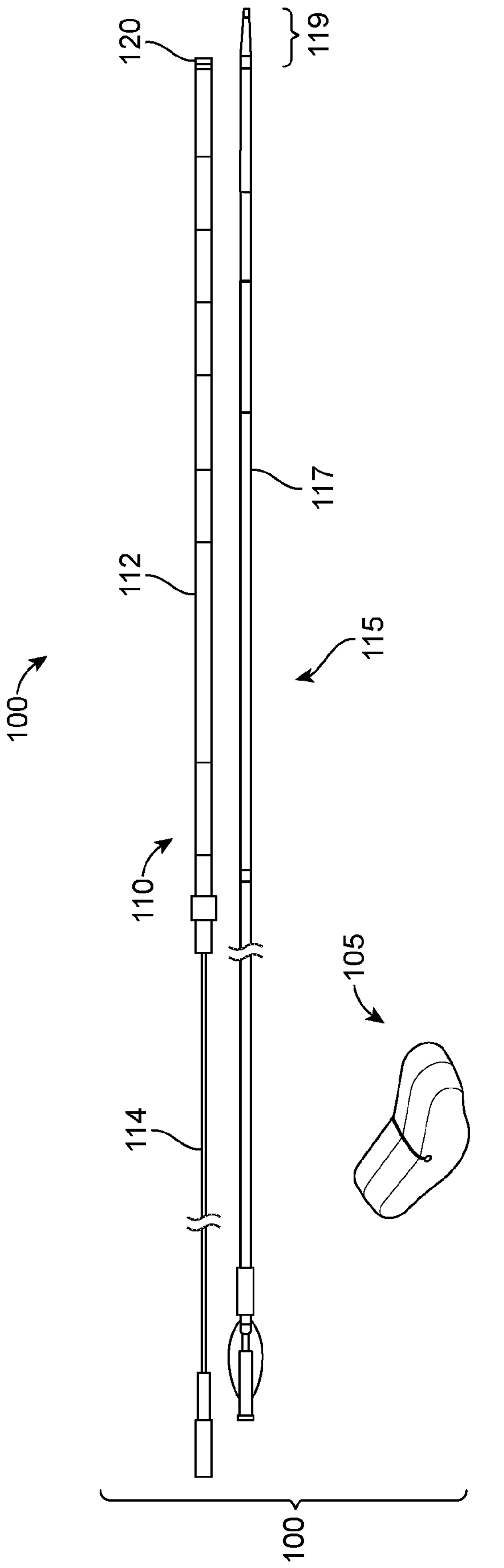
FIG. 1A is an exploded view of an intravascular system.

It should be appreciated that the drawings are for example only and are not meant to be to scale. It is to be understood that devices described herein may include features not necessarily depicted in each figure.

DETAILED DESCRIPTION

Some systems of intravascular access devices enable "monopoint" access. These systems are single-operator systems that allow the operator to work at a single proximal hub and, in the case of catheters having proximal rail segment that are not full-length catheters, can manipulate multiple (two or more) devices simultaneously to navigate through the intravascular anatomy with single-handed grasping or "pinches" of the proximal portion of the multiple devices. These pinches, however, can lead to inadvertent slippage between the components (e.g., devices, catheters, and/or the like). Slippage can cause the operator's desired assembled configuration for the components to be lost as they are advanced through tortuous anatomy leading to difficulties in navigation and procedural delays. Slippage can in some instances also cause injury to the patient. Delays and difficulties in intravascular navigation, especially for the treatment of acute stroke, can be particularly detrimental to a patient's health.

Consistent with implementations of the current subject matter, a coupler can be used with intravascular access systems, such as single-operator systems. The coupler can be removably affixed to at least a portion of multiple components (also referred to herein as "catheter components"), such as medical devices including catheters, guide wires, or the like, of the intravascular access system. The coupler accommodates different positions of the medical devices relative to one another during movement of the medical devices through the vasculature of the patient. For example, the coupler can help to maintain a locked engagement between the various medical devices relative to one another. The coupler can be applied to or removed from multiple devices by the user to couple or un-couple the devices at desired periods in the procedure. Thus, the coupler replaces the need for the user to "pinch" the devices together to retain their assembled configuration, and helps to prevent or limit slippage between the medical devices, thereby reducing or eliminating delays and difficulties in vascular navigation. Accordingly, the coupler can improve patient outcomes and improve the efficiency of intravascular procedures.

Additionally or alternatively, the coupler can include one or more structural features, such as a material, shape, or other design element (e.g., multiple components) of the coupler that makes it easy and/or simple to use in a quick and single-handed manipulation, and as a result improves the usability of the coupler. For example, as described herein, the coupler includes a material that is configured to be repeatedly deformed or flexed away from its set shape, yet be elastic enough to return to a position that maintains the position of the medical devices with respect to one another.

The coupler can additionally or alternatively include a shape that allows for the coupler to be easily gripped and/or a material having at least some tackiness. This allows for the coupler to be easily gripped by the operator and/or helps to prevent the medical devices from moving with respect to the surgery table or patient. As described herein, the coupler can be designed to be affixed to the table or patient as well as to the components being gripped, further reducing the likelihood of slippage of the coupler and/or between the medical devices.

Figure 1B:
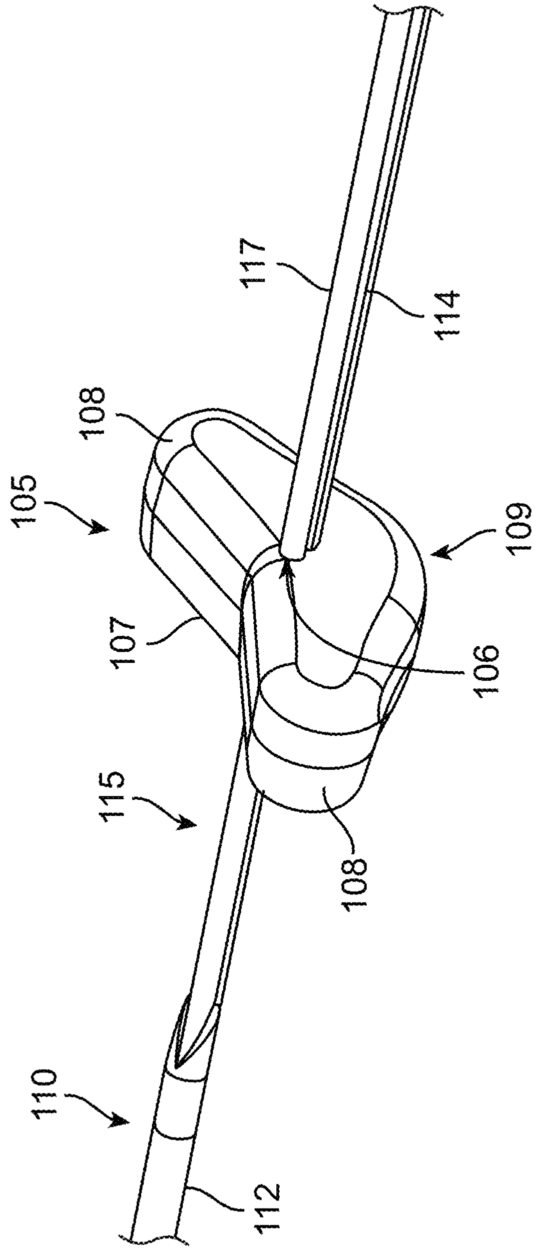
FIG. 1B is an assembled partial view of the system of FIG. 1A.

Described herein are intravascular access systems for the facilitation of intraluminal medical procedures within the vasculature that include at least one removable coupler. FIGS. 1A-1B are exploded and assembled views, respectively, of an example of an intravascular access system 100. The intravascular access system 100 includes an outer catheter 110 and an inner catheter 115, among other components. For example, the intravascular access system 100 can include one or more catheters, such as the outer catheter 110, the inner catheter 115, and/or additional catheters, such as an aspiration catheter. The aspiration catheter can have a single lumen, a proximal rotating hemostasis valve, and/or the like.

Additionally and/or alternatively, the intravascular access system 100 can include at least one coupler 105 consistent with implementations of the current subject matter. The configuration and components of the intravascular access system 100 can vary and is not intended to be limited only to the system 100 shown herein. The system 100 can include one or more components of the systems described in U.S. Pat. No. 11,224,450, which is incorporated by reference herein.

Also, while the intravascular access system 100 in FIGS. 1A and 1B is shown and described as being used with at least one coupler 105, other couplers described herein, such as the coupler 105, 305, 505, 605, 705, can be used with the intravascular access system 100. Further, the at least one coupler 105, 305, 505, 605, 705, can be the same or similar to one another. The at least one coupler 105, 305, 505, 605, 705, can include one or more components, properties, and/or features that are the same as and/or can be used and/or interchanged with one or more components, properties, and/or features of another one of the at least one coupler 105, 305, 505, 605, 705. Thus, while in some instances one of the at least one couplers 105, 305, 505, 605, 705 are described, the at least one coupler 105, 305, 505, 605, 705 can include at least one component, property, and/or feature of another one of the at least one coupler 105, 305, 505, 605, 705.

Generally and as shown in FIG. 1A, the outer catheter 110 can include a tubular distal portion 112 having a lumen and a proximal extension 114. The proximal extension 114 need not include a lumen. In some implementations, the proximal extension 114 is a hypotube or cut hypotube. The proximal extension 114 can alternately be a solid element, such as a metal or polymer wire or shaft having a round or oval cross-section or a metal ribbon having a square or rectangular cross-section. Accordingly, the outer catheter 110 can include an end (e.g., a proximal end) including a wire, a ribbon, and/or the like. The proximal extension 114 can be metal or another material that is a structurally suitable component that is stiff enough to push the outer catheter 110 through the anatomy and flexible enough to take on the turns of the vasculature that are encountered. The proximal extension 114 can have a smaller outer dimension than the tubular distal portion 112. The inner catheter 115 can include a flexible elongate body 117. The flexible elongate body 117 can be fully or partially tubular and is sized to insert within the lumen of the tubular distal portion 112 of the outer catheter 110. The inner catheter can be a delivery catheter having a tapered tip and a single lumen, and/or other configurations.

The coupler 105 is configured to be removably affixed to at least a portion of one or more components (or medical devices) of the system 100. The coupler 105 can be removably affixed to at least a portion of the proximal extension 114 and at least a portion of the flexible elongate body 117 of the inner catheter 115 to accommodate different relative positions between the outer catheter 110 and the inner catheter 115 during movement of the catheters 110, 115 through the vasculature. The coupler 105 can have a unitary elastic body with at least one slot 106 that is configured to receive and retain both the proximal extension 114 and the flexible elongate body 117 of the two catheters 110, 115 (see FIG. 1B).

One or more couplers 105, as described herein, can receive and/or maintain the relative positions of the one or more (e.g., one, two, three, four, or more) components (e.g., medical devices), which can help to reduce or eliminate unwanted delays during a procedure. Additional couplers can couple one or more components to components maintained by a first coupler. The additional couplers can be removable, fixed or slidably attached to the additional medical devices, and/or couple the additional medical devices to one or more of the medical devices maintained by the first coupler. Additionally and/or alternatively, the one or more medical devices can be received by a single coupler either in a single slot or multiple slots, or by multiple couplers to maintain these multiple components in an axially constrained configuration, such as during advancement within the vasculature. The coupler 105 is described below in greater detail.

The inner catheter 115 can be in a juxtaposition relative to the outer catheter 110 that provides an optimum relative extension between the two components for a single smooth advancement through the vasculature. The inner catheter 115 can be positioned through the lumen of the outer catheter 110 such that a distal end region 119 of the inner catheter 115 extends just beyond a distal-most end 120 of the outer catheter 110. The distal end region 119 of the inner catheter 115 can include a tapered section, which can eliminate the stepped transition between the inner catheter 115 and the outer catheter 110 as described in U.S. Pat. No. 11,224,450 thereby avoiding issues with catching on branching vessels within the region of the vasculature such that the outer catheter 110 may easily traverse angulated turns. The optimum relative extension, for example, can be the distal end region 119 of the elongate body 117 extending just distal to the distal-most end 120 of the outer catheter 110. A length of the distal end region 119 extending distal to the distal-most end 120 of the outer catheter 110 during advancement can be between about 0.5 cm and about 4 cm. This juxtaposition can be a locked engagement achieved by the coupler 105.

The coupler 105 can couple to one or more of the outer catheter 110 (e.g., the proximal extension 114 of the outer catheter 110), and the inner catheter 115 (e.g., the flexible elongate body 117 of the inner catheter 115) The coupler 105 can be slidable along at least a length of the system components when coupled so that the mechanical attachment is adjustable. This allows for the relative position of the clamped components to be changed, if desired, while the mechanical clamping of the coupler 105 is occurring. The difference is that the relative position is changeable when desired by a user as opposed to inadvertently due to slippage of the coupling provided. The clamping position of the coupler 105 can be changed from engaging with a first combination of components to a different combination of components. For example, the system 100 can additionally include a guidewire (not shown). The guidewire extends through the lumen of the inner catheter 115 and the inner catheter 115 extends through the outer catheter 110 and can be selectively coupled and uncoupled with one or more of inner catheter 115 and outer catheter 110.

The coupler 105 can clamp together the inner catheter 115 and the outer catheter 110 during a first step of a method. The inner catheter 115 can be removed from the system, for example, upon achieving a particular location within the vasculature, leaving the outer catheter 110 and the guidewire. The outer catheter 110 and the guidewire can then be clamped in fixed arrangement by the coupler 105 either within the slot 106 used by the outer and inner catheters or by a different slot within the coupler 105. The coupler 105 can affix to one or more components of a system (e.g., the system 100) depending on what phase of the method is being performed and what components are inserted within the vasculature. Whether the relative position of the system components is fixed by the coupler, a combination of couplers, or by a user, the proximal end of the system components are configured to be held at a single point by a user.

The couplers 105 described herein can be part of a catheter system that facilitates any of a variety of medical procedures within the vasculature and need not be limited to the system 100 shown in FIGS. 1A-1B. The coupler 105 can be removably affixed to at least a portion of the proximal ends of both first and second medical devices (e.g., at least two components) that are in nested arrangement with one another. The coupler 105 can axially affix the two medical devices together during movement of the system in the vasculature. As an example, a first medical device having a proximal end portion and a distal end portion with a lumen can have a second medical device inserted through its lumen. The removable coupler can be attached to at least a portion of the proximal ends of both of the first and second medical devices to axially affix the first and second medical devices with respect to one another. The first and second medical devices affixed by the unitary elastic body of the coupler can be moved together within the vasculature.

In an implementation, the coupler 105 can be an elastomeric spring clip configured to be flexed from a resting, "locked" or clamped configuration where the coupler 105 and the component are in clamped engagement with one another and a flexed, "unlocked" or unclamped configuration where the component may be removed from engagement with the coupler 105. The coupler 105 can be formed of unitary solid piece of material such as silicone rubber, elastomeric polyurethane, thermoplastic elastomer, or another polymer that is configured to be repeatedly deformed or flexed away from its set shape. The solid coupler 105 provides a surface area of the coupler equal to the entire surface in contact with the component for maximum friction and holding force. However, the coupler 105 can alternatively be hollow. The coupler material can be soft enough to be flexed by a user to widen (e.g., manually actuate) the slot 106 and elastic enough to return to a closed position when the opening force is removed. The material can have at least some tackiness for grip. The elastomeric material can be in a Shore Hardness range of about 50 Shore A, 20-90 Shore A, or about 30-70 Shore A, or about 40-60 Shore A.

Figure 2A:
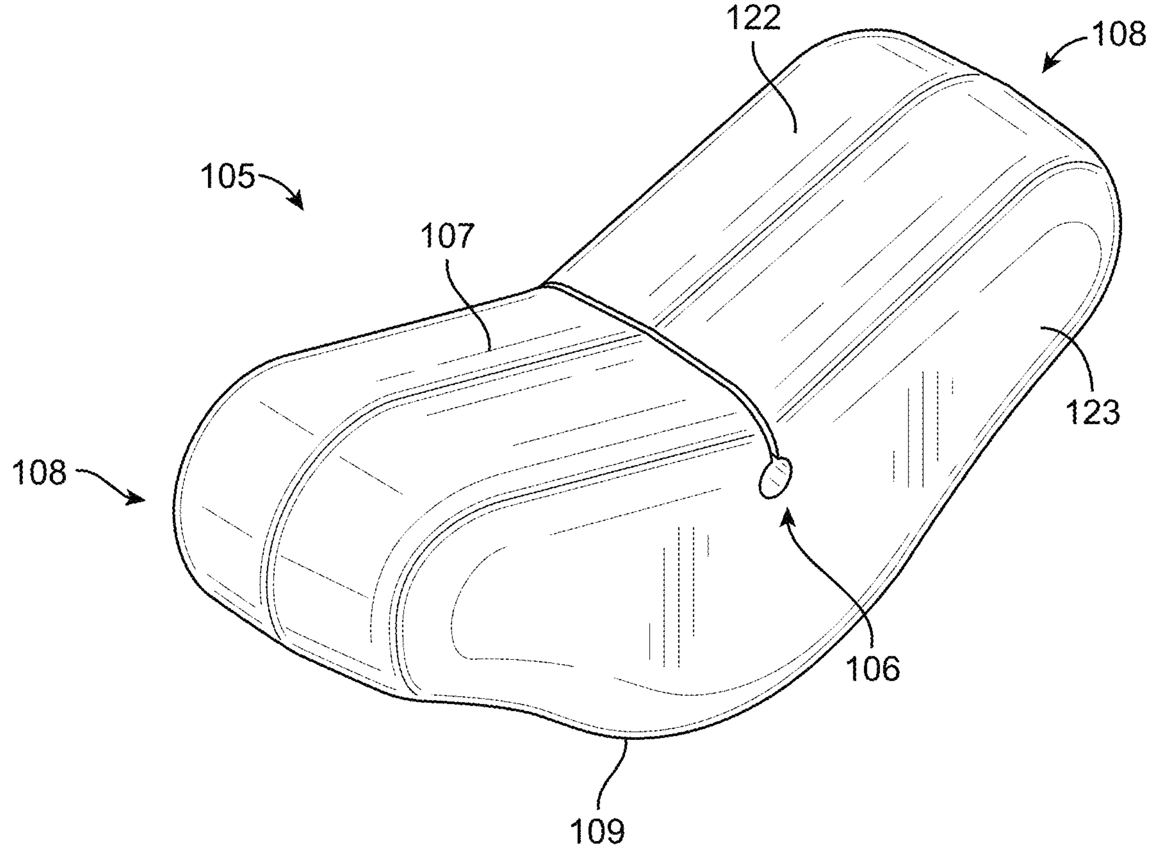
FIG. 2A is a perspective view of an implementation of a coupler.
Figure 2B:
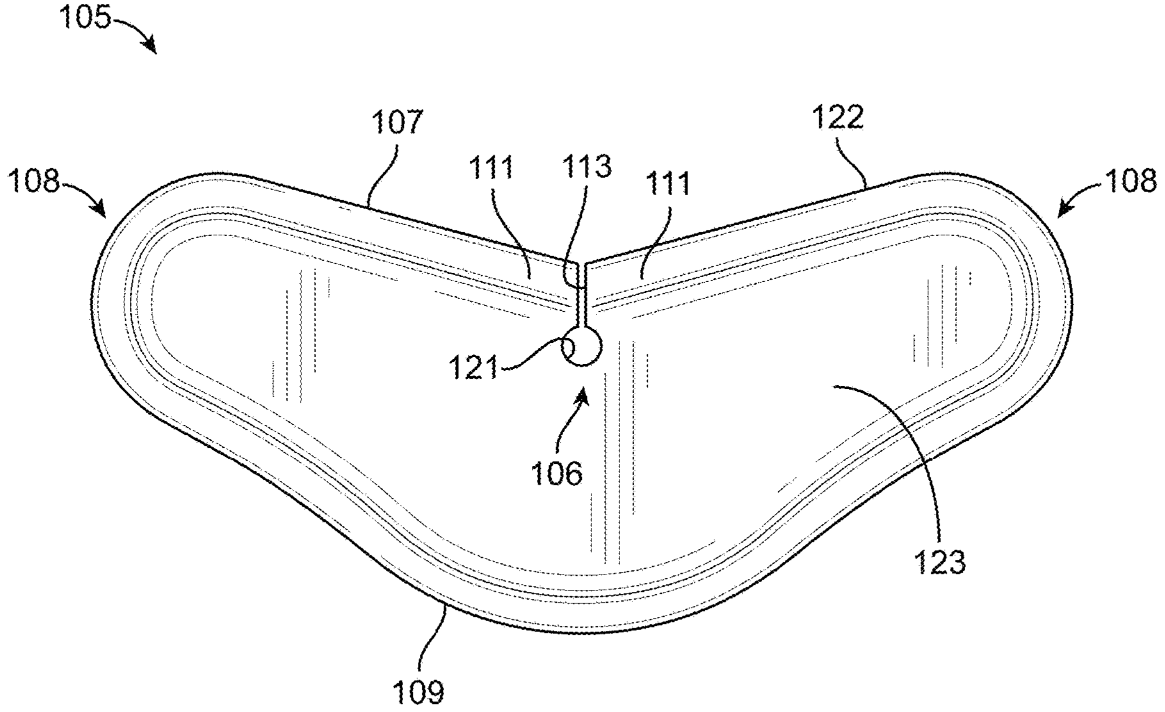
FIG. 2B is a front view of the coupler of FIG. 2A.
Figure 2C:
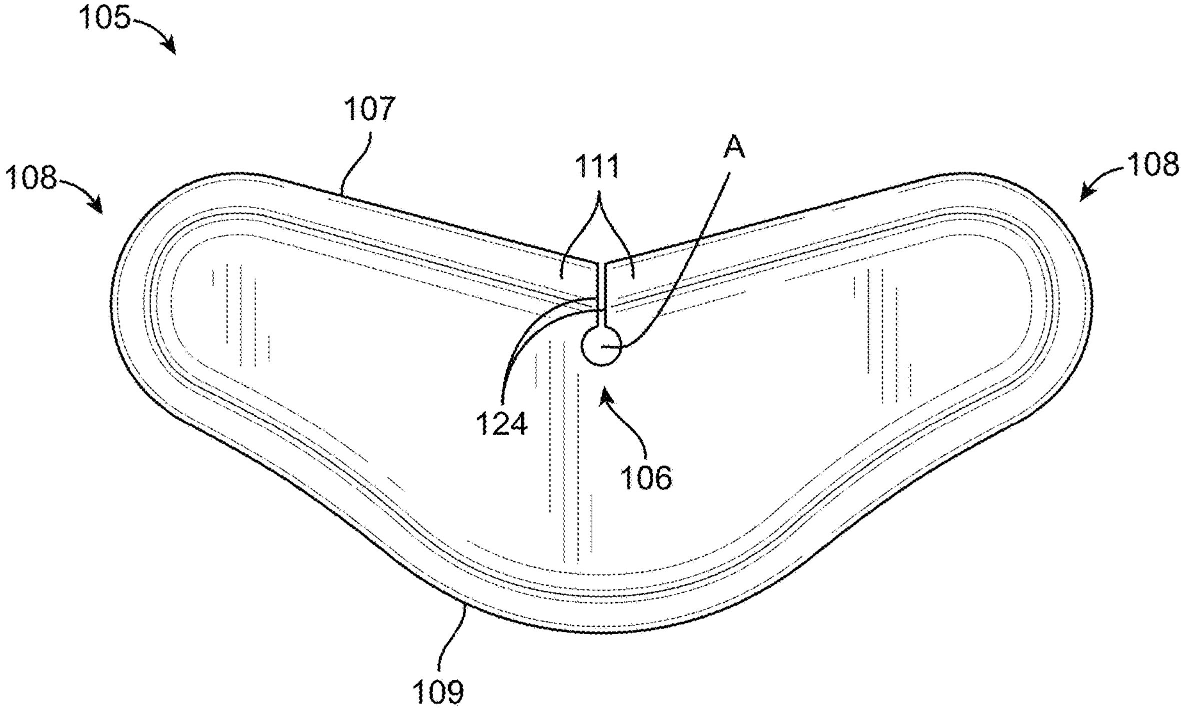
FIG. 2C is a rear view of the coupler of FIG. 2A.

As best shown in FIGS. 2A-2C, the coupler 105 can include a pair of wings 108 configured to be manipulated (e.g., manually actuated) by a user to open the coupler 105 (e.g., open the slot 106). The pair of wings 108 extend in direction laterally away from one another. The pair of wings 108 can be additionally or alternatively angled away from one another in the same longitudinal directional. The pair of wings 108 provide a shape to the coupler 105 that is substantially V-shaped shaped. The shape provided by to the coupler 105 by the pair of wings 108 also can be generally triangular-, chevron-, or heart-shaped. Regardless, the actual geometry, the coupler 105 is generally rounded rather than angular or having sharp corners. The positioning and/or shape of the pair of wings 108 allows for the operator to easily press the pair of wings 108 to open up slot 106 to insert or move one or more components to couple the coupler 105 to the one or more components and/or to adjust a position of the one or more components relative to one another and/or to the coupler 105. Opening of the slot 106 may allow for the one or more components to be inserted and/or removed from the coupler 105. Manual actuation of the wings 108 to open the slot 106 may be done against a table or other surface, such as a flat surface. The rounded geometry of the coupler 105 can also allow for the coupler 105 to be easily gripped by the operator.

The coupler 105 includes a lateral surface 122 and opposing side surfaces 123. The lateral surface 122 extends about a perimeter of the coupler 105. For example, the lateral surface 122 extends around an entire perimeter of the coupler 105. The lateral surface 122 can be smooth such that it does not include sharp corners about the perimeter of the coupler 105. The lateral surface 122 includes an upper surface 107 and a lower surface 109. The upper surface 107 extends along a valley (e.g., a valley portion) of the coupler 105, such as along a valley of the V shape. The lower surface 109 connects opposing ends of the upper surface 107 and extends along a remaining portion of the perimeter of the coupler 105. The lower surface 109 and the upper surface 107 can be integrally formed to define the lateral surface 122 of the coupler 105. The lower surface 109 and the upper surface 107 can smoothly transition between one another. The opposing side surfaces 123 can be connected by the lateral surface 122, which is positioned between the opposing side surfaces 123. The surface of the coupler 105 can smoothly transition between the lateral surface 122 and the opposing side surfaces 123.

The pair of wings 108 are movable relative to one another to widen or open the at least one slot 106. The slot 106 extends along the upper surface 107 of the valley of the V shape toward the lower surface 109 of the lateral surface 122 so that the slot 106 snap fits with at least one component of interest (i.e., proximal extension 114 of the outer catheter 110, flexible elongate body 117 of the inner catheter 115, and/or a guidewire). Referring to FIGS. 2B and 2C, the slot 106 includes an upper portion or upper end 113 and a lower end. The lower end can be formed with a circular cross-section or a tubular portion 121. When the coupler 105 is in the resting configuration, opposing arms 111 forming an upper end 113 of the slot 106 are positioned near one another and not touching one another so that the slot 106 is nearly fully tubular. For example, the opposing arms 111 include opposing flat surfaces 124 that are spaced apart from one another. The opposing flat surfaces 124 can be parallel to one another. The opposing flat surfaces 124 can form a sharp or rounded corner at an intersection with the upper surface 107. The opposing flat surfaces 124 can form a sharp or rounded corner at an intersection with the tubular portion 121. Such configurations can allow for the at least one component to be positioned within the tubular portion 121, while limiting or preventing movement of the at least one component to unintentionally slip or slide out of the tubular portion 121.

When the opposing arms 111 forming the upper end 113 of the slot 106 are positioned near one another any component positioned within the tubular portion 121 of the slot 106 is enclosed within the slot 106 (e.g., within the tubular portion 121) and the coupler 105 is "locked" onto the component. When the opposing arms 111 of the slot 106 are separated from one another such as upon flexing the coupler 105 so that the wings 108 rotate (e.g., rotate away from one another) relative to axis A (see, e.g., FIG. 2C), the component(s) can be removed from the slot 106. Thus, the space between the arms 111 (e.g., the opposing flat surfaces 124) in the resting "locked" configuration of the coupler 105 can be less than an outer diameter of the component being received in the slot 106 and the space between the arms 111 in the flexed "unlocked" configuration can be greater than the outer diameter of the component in the slot 106 so that the component can be withdrawn from the engagement. The slot 106 can have other shapes and configuration that correspond to the shapes of the components that are received in the slot 106. In the example of the system shown in FIG. 1B, the diameter of the tubular portion 121 is close to the outer diameter of the flexible elongate body 117 of the inner catheter 115, for example, having a slot tubular portion 121 with a diameter from about 70% to about 120% of the larger component's (in this system the flexible elongate body 117) outer diameter.

The components received within the slot 106 are generally elongate components extending along a longitudinal axis. The longitudinal axis of the components lie within the slot 106 such that the axis A of the slot 106 is substantially coaxial with the longitudinal axis of the components being received. In some implementations, the longitudinal axis of the components are parallel to the axis A of the slot 106 when the components are positioned within the slot 106. In some implementations, the proximal extension 114 of the outer catheter 110 can have a smaller outer diameter than the flexible elongate body 117 of the inner catheter 115. The lower tubular portion 121 of the slot 106 can be sized to receive both the proximal extension 114 and at least a portion of the flexible elongate body 117. Preferably, the smaller proximal extension 114 of the outer catheter 110 is positioned within the slot 106 relative to the flexible elongate body 117 of the inner catheter 115 so that it is between about 3 o'clock and 9 o'clock. This ensures that when the slot 106 widens to receive the outer diameter of the flexible elongate body 117 that the smaller sized proximal extension 114 is effectively held by the coupler 105 and unlikely to slide out the upper end 113 of the slot 106. As discussed above, the upper end 113 of the slot 106 defined by the opposing arms 111 widens to receive the outer diameter of the flexible elongate body 117. The opposing arms 111 while clamped onto the flexible elongate body 117 may not return to their resting state near one another and may remain at least partially flexed away from one another. Positioning the smaller diameter proximal extension 114 within the tubular portion 121 of the slot 106 preferably away from the 12 o'clock position prevents it from inadvertently coming out of clamping engagement with the coupler 105. The coupler 105 can be provided with multiple slots 106 for independently securing the one or more components rather than securing more than a single component in a single slot 106. Additionally and/or alternatively, the coupler 105 can be provided with multiple tubular sections 121 within one slot 106 of same or varying diameters.

The coupler 105 can be flexed with a single hand due to the shape of the coupler 105 being in the form of a V. The slot 106 extending along the upper surface 107 can be located within a valley of the V and two wings 108 can extend upward at an angle on either side of the valley. A user may press down on the two wings 108 to increase the angle of the wings 108 separating them from one another and flattening out the V shape, which in turn flexes the opposing arms 111 of the slot 106 away from one another thereby opening the slot 106. Releasing the two wings 108 results in their returning to the original angle and V shape, which in turn causes the arms 111 of the slot 106 to return to their resting position closer to one another closing the slot 106 at least partially around the component(s). A user may also flip the coupler 105 over and press onto the lower surface 109 of the coupler 105 to change the angle of the two wings 108, flatten out the V, and open the slot 106. The surfaces of the coupler 105 can be rounded and smooth to ensure comfort of the user when manually activating, squeezing or pressing on the coupler 105 to flex the coupler 105 into the unlocked configuration.

The coupler 105 provides the additional advantage of helping to prevent the proximal ends of the medical devices being clamped from sliding off the surgery table. In some implementations, the coupler 105 has a shape that prevents it from rolling relative to the table. The material of the coupler 105 may also be helpful in preventing inadvertent rolling relative to the table or the patient. The coupler 105 material may be relatively tacky so that it tends to grip to one or more of the table, drapes, or other fixture on the operating table. The coupler 105 can also be designed to affixed to the table or patient as well as to the components being gripped, such as with an adhesive or fastener such as a suction cup, hook and loop fastener, magnet, or clamp or clip type fastener.

The system 100 can also include two or more removable couplers 105 for coupling multiple pairs of components or for coupling the same two or more components at multiple longitudinal locations. The coupler 105 and at least one of the inner catheter 115 and the outer catheter 110 can be packaged together in a sterile package. The coupler 105 can be a disposable feature or reusable.

Figure 3:
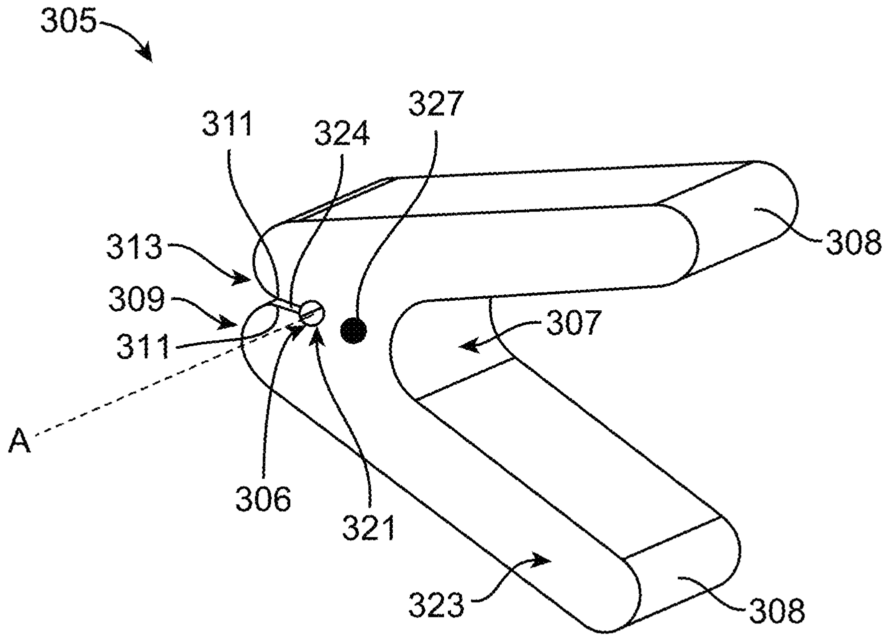
FIG. 3 is a perspective view of an implementation of a coupler.

FIG. 3 illustrates an example of a coupler 305. The coupler 305 can be the same as or similar to the coupler 105, or another coupler described herein. The coupler 305 includes a pair of wings (e.g., arms) 308 and at least one slot 306, which are functionally similar to the wings 108 and the at least one slot 106 of coupler 105. The pair of wings 308 can be additionally or alternatively angled away from one another in the same longitudinal directional. The pair of wings 308 can be elongated. The pair of wings 308 provide a shape to the coupler 305 that is substantially V-shaped. The shape provided by to the coupler 305 by the pair of wings 308 also can be generally triangular-, chevron-, or heart-shaped. Regardless, the actual geometry, the coupler 305 is generally rounded rather than angular or having sharp corners. The positioning and/or shape of the pair of wings 308 allows for the operator to easily grasp the pair of wings 308 to open slot 306 and allow the user to couple two or more components together and/or to adjust a position of the one or more components relative to one another and/or to the coupler 305.

The pair of wings 308 are movable relative to one another to widen or open the at least one slot 306. The slot 306 extends along the lower surface 309 opposite the valley of the V shape toward the upper surface 307 of the lateral surface 322 so that the slot 306 snap fits with at least one component of interest (i.e., proximal extension 114 of the outer catheter 140, flexible elongate body 117 of the inner catheter 115, and/or a guidewire). Referring to FIG. 3, the slot 306 includes an upper portion or upper end 313 and a lower end. The lower end can be formed with a circular cross-section or a tubular portion 321. When the coupler 305 is in the resting configuration, opposing arms 311 forming an upper end 313 of the slot 306 are positioned near one another and not touching one another so that the slot 306 is nearly fully tubular. For example, the opposing arms 311 include opposing surfaces 324 that are spaced apart from one another. The opposing surfaces 324 can be parallel to one another. The opposing surfaces 324 can be flat or rounded. The opposing surfaces 324 can form a rounded corner at an intersection with the lower surface 309. The opposing surfaces 324 can form a sharp or rounded corner at an intersection with the tubular portion 321. Such configurations can allow for the at least one component to be positioned within the tubular portion 321, while limiting or preventing movement of the at least one component to unintentionally slip or slide out of the tubular portion 321.

When the opposing arms 311 forming the upper end 313 of the slot 306 are positioned near one another any component positioned within the tubular portion 321 of the slot 306 is enclosed within the slot 306 (e.g., within the tubular portion 321) and the coupler 305 is "locked" onto the component. When the opposing arms 311 of the slot 306 are separated from one another such as upon pushing, squeezing, or otherwise manipulating the coupler 305 so that the wings 308 rotate (e.g., rotate towards one another) relative to axis A (see, e.g., FIG. 3), the component can be removed from the slot 306. For example, the pair of wings 308 may be compressed towards one another to cause the opposing arms 311 to widen apart about hinge point 327. This allows for the component to be removed from the slot 306. Thus, the space between the arms 311 in the resting "locked" configuration of the coupler 305 can be less than an outer diameter of the component being received in the slot 306 and the space between the arms 311 in the flexed "unlocked" configuration can be greater than the outer diameter of the component in the slot 306 so that the component can be withdrawn from the engagement. The slot 306 can have other shapes and configuration that correspond to the shapes of the components that are received in the slot 306.

The coupler 305 can be flexed with a single hand due to the shape of the coupler 305 being in the form of a V. The slot 306 extending along the lower surface 309 can be located opposite the valley of the V and two wings 308 can extend upward at an angle on either side of the valley. A user can press on the two wings 308 to decrease the angle of the wings 308 separating them from one another, which in turn flexes the opposing arms 311 of the slot 306 away from one another thereby opening the slot 306. Releasing the two wings 308 results in their returning to the original angle and V shape, which in turn causes the arms 311 of the slot 306 to return to their resting position closer to one another closing the slot 306 at least partially around the component (s).

The coupler 305 provides the additional advantage of helping to prevent the proximal ends of the medical devices being clamped from sliding off the surgery table. For example, the coupler 305 can at least have flat opposing side surfaces 323 that prevents it from rolling relative to the table.

As with the previous embodiment 105, the coupler 305 can be manufactured from an elastomeric material which can be deformed, e.g. when the user opens up slot 306 by squeezing wings 308 together, but then springs back to the normal state when the wings are released. The elastomeric material can be in a Shore Hardness range of about 50 Shore A, or 20-90 Shore A, or about 30-70 Shore A, or about 40-60 Shore A.

Figure 4:
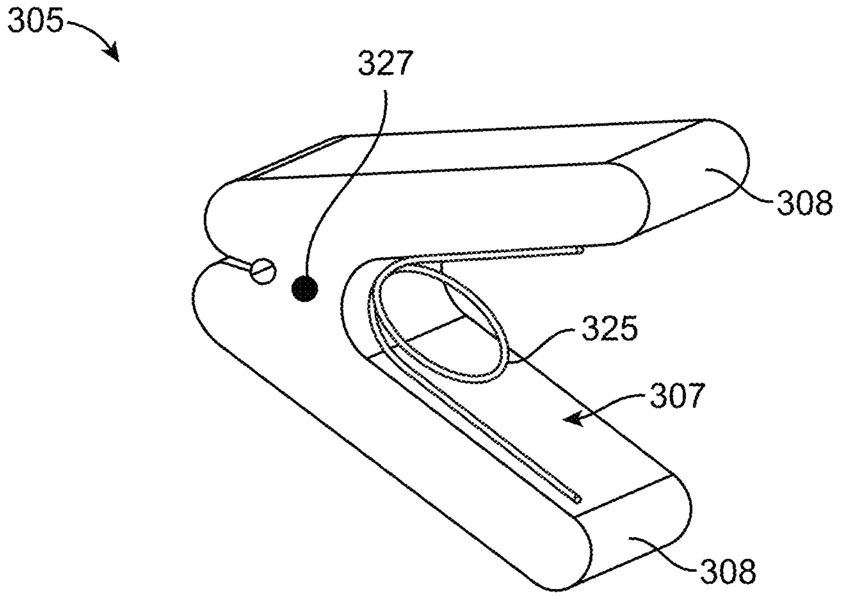
FIG. 4 is a perspective view of an implementation of a coupler.

FIG. 4 illustrates another example of the coupler 305. In this example, the coupler 305 includes a resilient member, such a spring 325, to increase the closing force of the coupler. The spring 325 comprises a coiled spring, leaf spring, or other spring member. The spring 325 can be coupled to a surface of the coupler 305, such as to the lateral surface 322. The spring 325 can be integrally formed with the pair of wings 308 or another portion of the coupler 305. Alternately the spring can be mechanically snapped into place, adhesive bonded, heat-staked, or otherwise attached to the coupler 305. The spring 325 can be positioned within the valley of the V. For example, the spring is coupled to the upper surface 307 such that it is positioned between the pair of wings 308. The spring 325 has the effect of pushing the pair of wings 308 away from one another when the coupler 305 is in the resting, "locked" configuration, thereby. increasing the grip force on the arms 311 to increase the coupling force on the components in slot 306.

Figure 5:
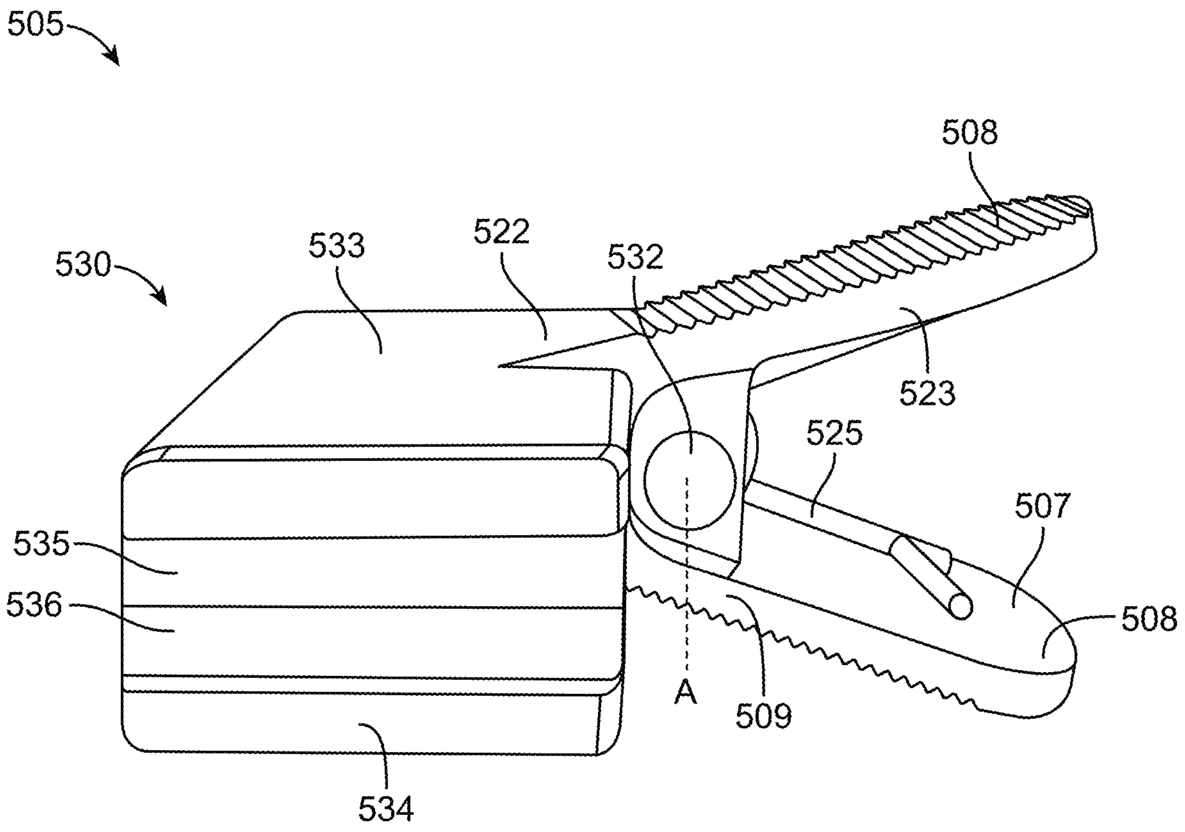
FIG. 5 is a perspective view of an implementation of a coupler.

FIG. 5 illustrates an example of a coupler 505. The coupler 505 can be the same as or similar to the coupler 105, or another couple described herein. The coupler 505 includes a pair of wings (e.g., arms) 508, which is similar to the pair of wings 108, 308.

The coupler 505 includes a lateral surface 522 and opposing side surfaces 523. The lateral surface 522 extends about at least a portion of a perimeter of the coupler 505. For example, the lateral surface 522 extends around a perimeter of the coupler 505. In some implementations, the lateral surface 522 is smooth such that it does not include sharp corners about the perimeter of the coupler 505. The lateral surface 522 includes an upper surface 507 and the lower surface 509. The upper surface 507 extends along a valley (e.g., a valley portion) of the coupler 505, such as along a valley of the V shape. The lower surface 509 extends along a remaining portion of the perimeter of the coupler 505. The lower surface 509 and the upper surface 507 can be integrally formed to define the lateral surface 522 of the coupler 505. The lower surface 509 and the upper surface 507 can smoothly transition between one another. The opposing side surfaces 523 can be connected by the lateral surface 522, which is positioned between the opposing side surfaces 523. The surface of the coupler 505 can smoothly transition between the lateral surface 522 and the opposing side surfaces 523. In other implementations, such as is shown in FIG. 5, the lateral surface 522 and the opposing side surfaces 523 can intersect at a sharp corner.

The coupler 505 includes a clamp 530. The clamp 530 is positioned at an opposite end of the coupler 505 relative to the pair of wings 508. The clamp 530 includes opposing first and second clamp portions (e.g., jaws) 533, 534. The first and second clamp portions 533, 534 are movable relative to one another. The clamp 530 may be defined by a slot, such as any of the slots described herein.

In some implementations, the first clamp portion 533 is integrally formed with and/or coupled to a first wing of the pair of wings 508 and the second clamp portion 534 is integrally formed with and/or coupled to a second wing of the pair of wings 508. The first clamp portion 533 and the respective first wing together form a first part of the coupler 505 and the second clamp portion 533 and the respective second wing together form a second part of the coupler 505. The first part and the second part can be coupled via a hinge 532. The hinge 532 allows for the first part and the second part to rotate about an axis A with respect to one another. The hinge 532 can include a hinge pin or other mechanism for allowing rotation between the first part and the second part.

For example, the pair of wings 508 are movable relative to one another to widen or open clamp 530. This allows for at least one component of interest (i.e., proximal extension 114 of the outer catheter 140, flexible elongate body 117 of the inner catheter 115, and/or a guidewire) to be positioned within the clamp 530 between the first clamp portion 533 and the second clamp portion 534. The first clamp portion 533 and the second clamp portion 534 can be parallel to one another. For example, the first clamp portion 533 and the second clamp portion 534 each include an inner surface that faces towards one another. The first clamp portion 533 and the second clamp portion 534 can be rectangular, although the first clamp portion 533 and the second clamp portion 534 can include other shapes, such as oval-, square-, or circular-shaped.

In some implementations, the clamp 530 includes a first clamp insert 535 and a second clamp insert 536. The first clamp insert 535 is coupled to the first clamp portion 533. The first clamp insert 535 is positioned on the inner surface of the first clamp portion 533. The second clamp insert 536 is coupled to the second clamp portion 534. The second clamp insert 536 is positioned on the inner surface of the second clamp portion 534. The first clamp insert 535 and the second clamp insert 536 can have a shape that is approximately the same as the respective first clamp portion 533 and the second clamp portion 534. The first clamp insert 535 and the second clamp insert 536 include a material, such as a foam, an elastomer, or the like. The material of the first clamp insert 535 and the second clamp insert 536 allows for the components to be held between the first clamp insert 535 and the second clamp insert 536 while limiting or preventing slipping of the components. The material of the first clamp insert 535 and the second clamp insert 536 can have a desired friction to limit movement of the components positioned between the first clamp insert 535 and the second clamp insert 536.

When the opposing clamp portions 533, 534 are positioned parallel to one another, any component positioned within between the opposing clamp portions 533, 534 is enclosed within the clamp 530 (e.g., between the first and second clamp inserts 535, 536) and the coupler 505 is "locked" onto the component. When the opposing clamp portions 533, 534 are separated from one another such as upon pushing, squeezing, or otherwise manipulating the coupler 505 so that the wings 508 rotate (e.g., rotate towards one another) relative to axis A (see, e.g., FIG. 5), the component can be removed from the clamp 530. The components can be positioned in any location or orientation between the opposing clamp portions 533, 534, such as between the first and second clamp inserts 535, 536.

The coupler 505 can be flexed with a single hand due to the shape of the coupler 505 being in the form of a V. For example, a user can press on the two wings 508 to decrease the angle of the wings 508 separating them from one another, which in turn flexes the opposing clamp portions 533, 534 of the clamp 530 away from one another thereby opening the space between the clamp portions 533, 534. Releasing the two wings 508 results in their returning to the original angle and V shape, which in turn causes the clamp portions 533, 534 to return to their resting position closer to one another closing the clamp 530 at least partially around the component(s).

Again referring to FIG. 5, the coupler 505 includes a resilient member, such a spring 525. The spring 525 include a coiled spring, leaf spring, or other spring member. The spring 525 can be coupled to a surface of the coupler 505, such as to the wings 508. The spring 525 can be integrally formed with the pair of wings 508 or another portion of the coupler 505. The spring 525 can be positioned within the valley of the V. For example, the spring is coupled to the upper surface 507 such that it is positioned between the pair of wings 508. The spring 525 increases the grip force required to move the pair of wings 508 towards one another. Additionally or alternatively, the spring 525 increases the grip force required to separate the first and second clamp portions 533, 534 to release the one or more components from the clamp 530. For example, moving the pair of wings 508 towards one another compresses at least a portion of the spring 525, increasing the grip force. In some implementations, the spring 525 biases the coupler in the locked position. For example, the spring 525 can push the pair of wings 508 away from one another when the coupler 505 is in the resting, "locked" configuration. This helps to limit or prevent unintentional slippage of the components positioned within the clamp 530. The spring force can be provided such that a sufficient clamping force is exerted on the components to couple them together and/or prevent or limit slippage of the components, without providing unnecessary compression force on the components.

Note that the total clamping force of clamp 530 on the components is related to both the force of spring 525 and the width of each of the first and second clamp portions 533 and 534. To limit the normal force on the components to avoid damaging them, but maintain a high total clamping force, the width of each clamp portion can be as wide as practical for this component. This concept of widening surface area of the clamping surface can be applied to previous embodiments.

Figure 6A:
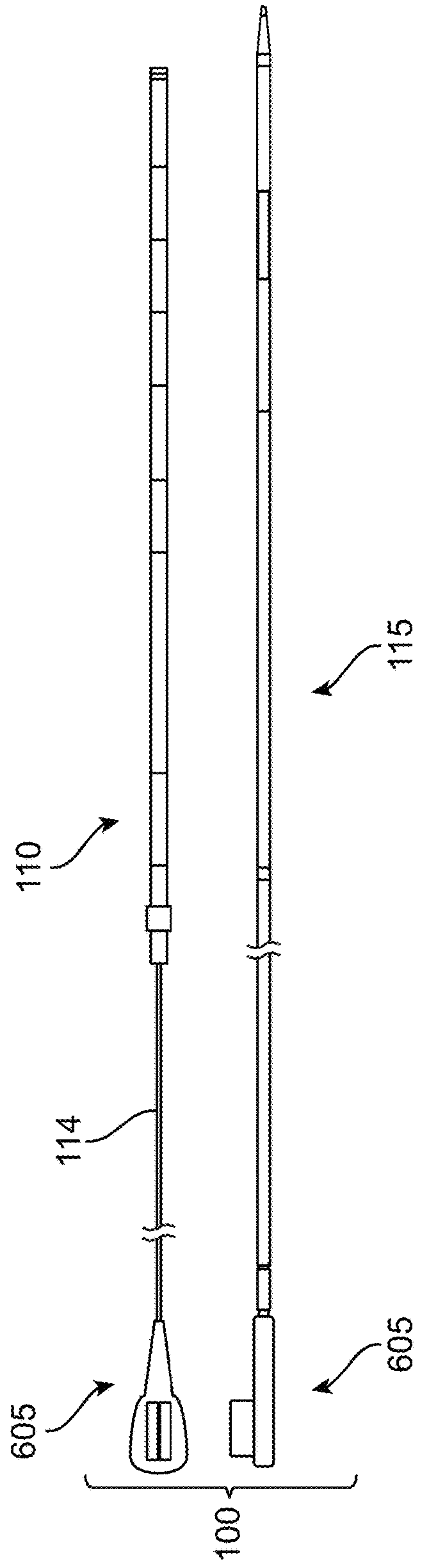
FIG. 6A is an exploded view of an implementation of a coupler.
Figure 6C:
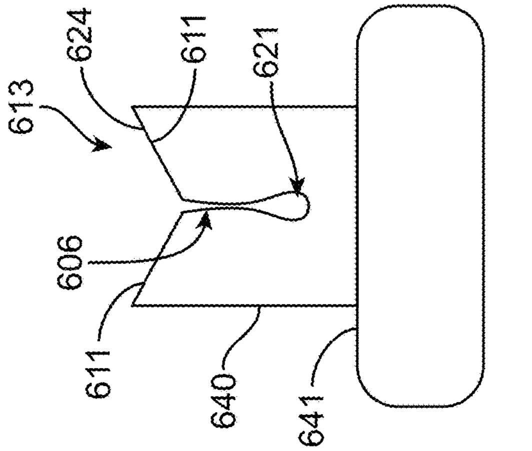
FIG. 6C is a front view of the coupler of FIG. 6A.
Figure 6B:
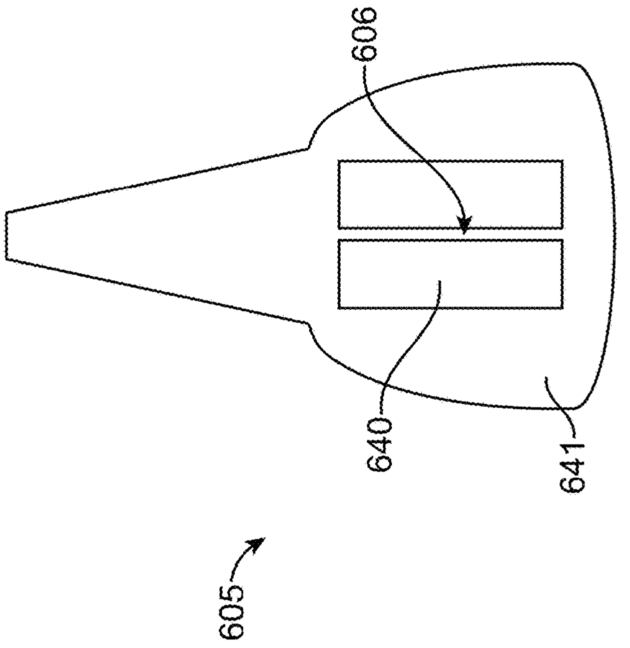
FIG. 6B is a top view of the coupler of FIG. 6A.

FIG. 6A-6C illustrate an example of a coupler 605. In this embodiment, the coupler 605 is integrally formed with and/or molded to a catheter component of the system 100, such as the outer catheter 110, the inner catheter 115, a guide wire, or the like. For example, as shown in FIG. 6A, the coupler 605 can be integrally formed with the proximal extension 114 of the outer catheter 110. The coupler 605 in this example can have one or more coupling features (e.g., a fastener, a clip, a slot, a snap-fit arrangement or the like) that couples one component (e.g., the outer catheter 110) to another component (e.g., the inner catheter 115, a guide wire, or the like). The coupler 605 can form a tab component (e.g., a coupling feature) of the one or more catheter components.

Referring to FIGS. 6B and 6C, the coupler 605 includes one or more coupling features 640 (e.g., a fastener, a clip, a slot, a snap-fit arrangement or the like) that couples one component (e.g., the outer catheter 110) to another component (e.g., the inner catheter 115, a guide wire, or the like). The coupling features 640 extends from a surface 641, such as a flat surface. The surface 641 can form at least a portion of the catheter component on which the coupler 605 is coupled and/or formed with. The coupling features 640 include at least one slot 606, which is the same as or similar to the at least one slot 106 or another slot described herein. The slot 606 can couple with (e.g., fasten, click onto, snap onto, or the like) another catheter component, such as the outer catheter 110 or the inner catheter 115. The coupler 605 including coupling features 640 can be constructed from an elastomeric material, such as a rigid, hard, or deformable elastomer, a plastic (e.g., high density polyethylene) or the like.

The slot 606 includes an upper portion or upper end 613 and a lower end. The lower end can be formed with a circular cross-section or a tubular portion 621. When the coupler 605 is in the resting configuration, opposing arms 611 forming the upper end 613 of the slot 606 are positioned near one another and not touching one another so that the slot 606 is nearly fully tubular. For example, the opposing arms 611 include opposing surfaces 624 that are spaced apart from one another. The opposing surfaces 624 can be parallel to one another. The opposing surfaces 624 can be flat or rounded. The opposing surfaces 624 can form a sharp or rounded corner at an intersection with the tubular portion 621. Such configurations can allow for the at least one catheter component to be positioned within the tubular portion 621, while limiting or preventing movement of the at least one component to unintentionally slip or slide out of the tubular portion 621.

When the opposing arms 611 forming the upper end 613 of the slot 606 are positioned near one another any component positioned within the tubular portion 621 of the slot 606 is enclosed within the slot 606 (e.g., within the tubular portion 621) and the coupler 605 is "locked" onto the component. To couple the coupling features 640 to a catheter component, the catheter component can be pushed into the engagement with the slot 606 of the coupling features 640. When the opposing arms 611 of the slot 606 are separated from one another such as upon pulling the catheter component away from the slot 606 of the coupling features 640, such as in a direction perpendicular to a longitudinal axis of the component formed with the coupler 605, the catheter component positioned within the slot 606 can be removed from the slot 606. Thus, the space between the arms 611 in the resting "locked" configuration of the coupler 605 can be less than an outer diameter of the component being received in the slot 606 and the space between the arms 611 in the flexed "unlocked" configuration can be greater than the outer diameter of the component in the slot 606 so that the component can be withdrawn from the engagement. The slot 606 can have other shapes and configuration that correspond to the shapes of the components that are received in the slot 606.

Figure 7:
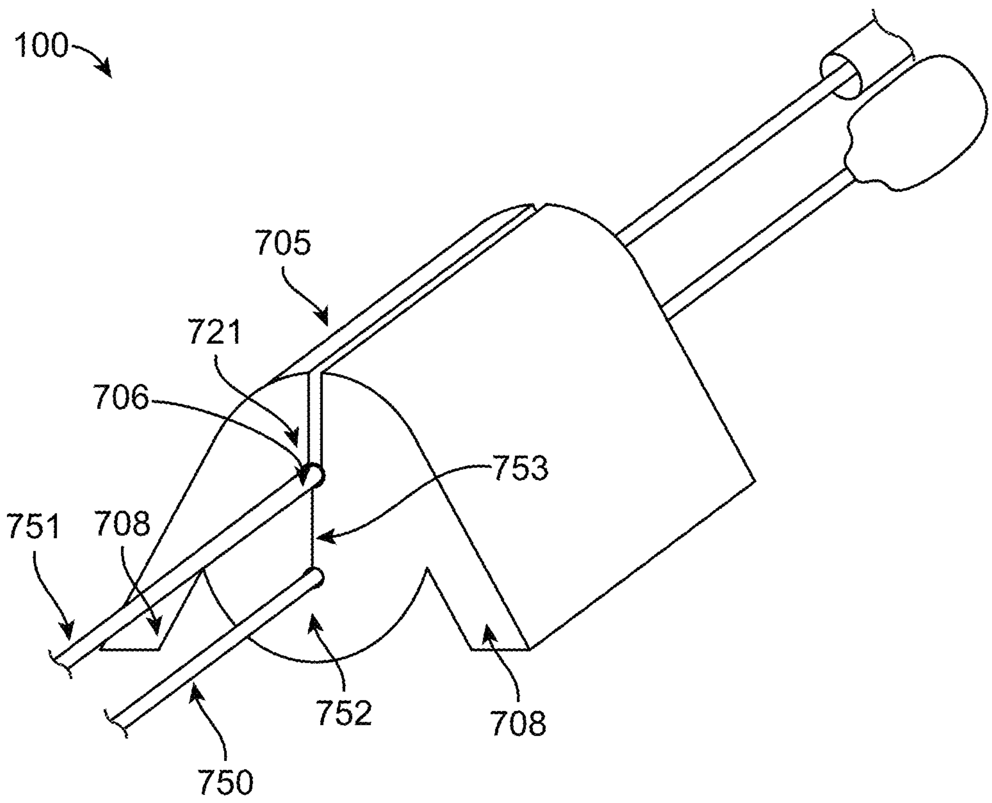
FIG. 7 is an assembled partial view showing an intravascular system including an implementation of a coupler.

FIG. 7 shows an example of the intravascular access system 100, which includes a coupler 705 that is similar in function to other couplers described herein. In this example, rather than the coupler 705 being a separate component, as in coupler 105, or fixed to a portion of a catheter component such as the proximal extension 114 of the outer catheter 110, as in coupler 605, the coupler 705 is slidably attached to one of the catheter components. In some examples, the coupler 705 is slidably attached to the proximal extension 114, but is not removable from the proximal extension 114. In other words, the coupler 705 may slide along the proximal extension 114, while the coupler 705 may be slidably and/or removably attached to one of the catheter components. For example, the coupler 705 is be slidable along at least a portion of a first catheter component 750 (e.g., the proximal extension 114 of the outer catheter 110, the flexible elongate body 117 of the inner catheter 115 and/or a guide wire) and/or a second catheter component 751 (e.g., the proximal extension 114 of the outer catheter 110, the flexible elongate body 117 of the inner catheter 115 and/or a guide wire). This configuration allows the coupler 705 to be placed at any position along the first catheter component 750 or the second catheter component 751 during use. This configuration also allows the coupler 705 and/or the position of the first catheter component 750 or the second catheter component 751 to be moved during different stages of the vascular procedure.

Referring to FIG. 7, the coupler 705 can include a slot 706, which is the same as or similar to any slot described herein. For example, the coupler 705 includes a pair of wings (e.g., arms) 708 and the slot 306, which are functionally similar to the wings 108 and the at least one slot 106 of coupler 105 and/or the wings 308 and the at least one slot 306. A tubular portion 721 (which can be the same as or similar to the other tubular portions described herein) of the slot 706 can include a connector 753 that connects a second slot 752 with the tubular portion 721 of the slot 706. The connector 753 can be a slit or other opening that allows for passage of at least one of the catheter components 750, 751. For example, a first one of the catheter components 750, 751 can slide through the slot 706, through the connector 753, and into the second slot 752, while another one of the catheter components 750, 751 can be positioned within the slot 706.

When opposing arms forming an upper end of the slot 706 are positioned near one another any component positioned within the tubular portion 721 of the slot 706 and/or within the second slot 752 is enclosed and the coupler 705 is clamped onto the components. When the opposing arms of the slot 706 are separated from one another, the catheter component positioned within the slot 706 and/or the second slot 752 can be removed from the slot 706 and/or the second slot 752 (e.g., via the connector 753). In this unclamped position, the coupler 705 can be positioned and/or repositioned, such as by sliding the coupler 705 along an axis parallel to the catheter components and along at least one of the catheter components. For example, a user can press on the two wings 708 to decrease the angle of the wings 708, which in turn flexes the opposing arms of the slot 706 away from one another thereby opening the slot 706. Releasing the two wings 708 results in their returning to the original angle, which in turn causes the arms of the slot 706 to return to their resting position closer to one another closing the slot 706 at least partially around the component(s).

Thus, the space between the arms in the resting clamped configuration of the coupler 705 can be less than an outer diameter of the component being received in the slot 706 and/or the second slot 752 and the space between the arms in the flexed unclamped configuration can be greater than the outer diameter of the component in the slot 706 and/or the second slot 752 so that the component can be withdrawn from the engagement. The slot 706 and/or the second slot 752 can have other shapes and configuration that correspond to the shapes of the components that are received in the slot 706 and/or the second slot 752.

Figure 8A:
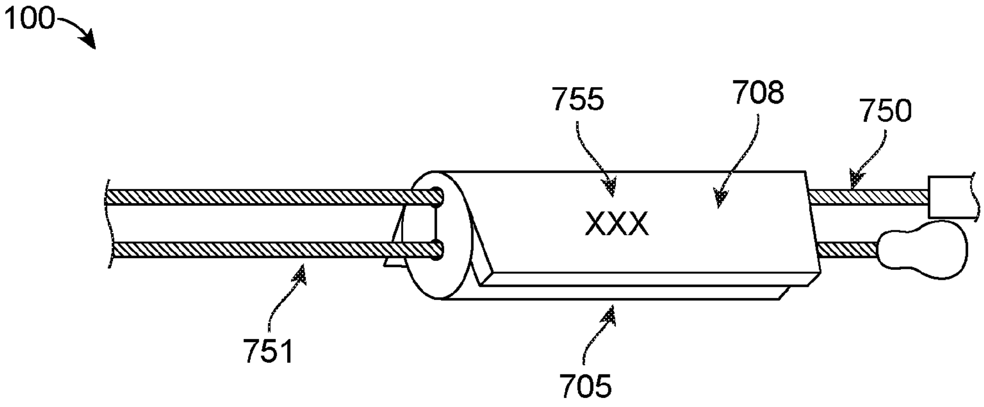
FIG. 8A is an assembled partial view showing an intravascular system including an implementation of a coupler.
Figure 8B:
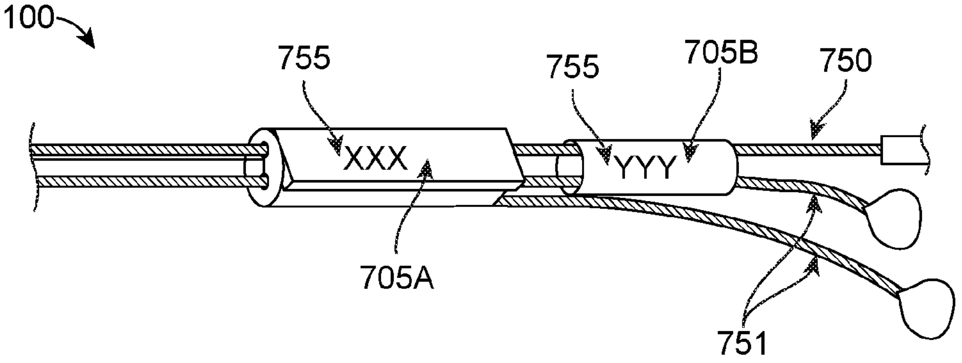
FIG. 8B is an assembled partial view showing an intravascular system including an implementation of a coupler.

In some implementations, the coupler 705 includes an identifier 755. For example, FIG. 8A shows an example of the coupler 705 including the identifier 755. The identifier 755 can include a marking, text, or the like that is positioned on an exterior of the coupler 705. The identifier 755 can indicate at least one of the catheter components (e.g., catheter components 751, 750) that the coupler 705 is affixed to and/or is coupled to, for example the size of the catheter component. FIG. 8B illustrates an example of the system 100 including a plurality of couplers 705. For example, the system 100 can include a first coupler 705A and a second coupler 705B. Each of the couplers 705A, 705B can correspond to the size and/or model of the particular catheter component to which it is affixed or coupled to. For example, each of the couplers 705A, 705B can have different identifiers 755 indicating at least one of the catheter components (e.g., catheter components 751, 750) that the particular coupler 705A, 705B is affixed to and/or is coupled to. In this manner, the coupler 705 helps to identify which device is which to reduce confusion when using multiple size catheter components simultaneously.

Figure 9:
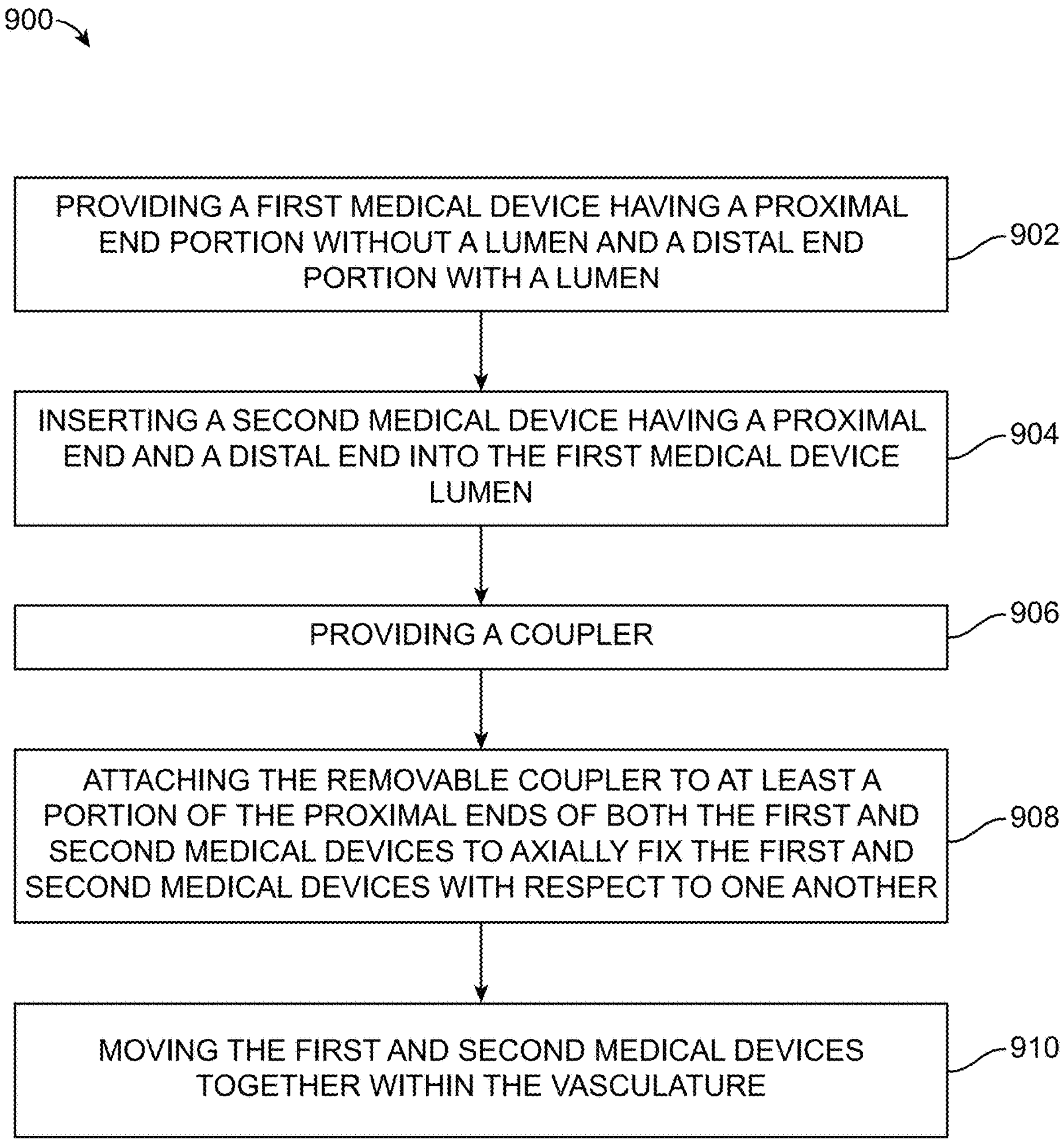
FIG. 9 is an example process for performing a medical procedure within a vasculature.

FIG. 9 illustrates a method 900 of performing a medical procedure within the vasculature. The method 900 can be performed using any of the couplers described herein, such as the coupler 105, 305, 505, 605, 705.

At 902, a first medical device is provided. The first medical device can include a proximal end portion without a lumen and a distal end portion with a lumen. The first medical device can include at least one catheter component, such as an outer catheter 110, a proximal extension 114 of the outer catheter 110, an inner catheter 115, a flexible elongate body 117 of the inner catheter 115, or the like.

At 904, a second medical device is inserted into the lumen of the first medical device. The second medical device can include a proximal end and a distal end. The second medical device can include at least one catheter component, such as an outer catheter 110, a proximal extension 114 of the outer catheter 110, an inner catheter 115, a flexible elongate body 117 of the inner catheter 115, or the like.

At 906, a coupler is provided. The coupler can be removable, fixed to at least one of the first medical device or the second medical device or slidably attached to at least one of the first medical device or second medical device. The coupler can include a unitary elastic body with at least one slot. The slot can receive and retain the proximal ends of the first and second medical devices. The coupler can include a clamp that can receive and retain at least a portion of the first and second medical devices, such as the proximal ends of the first and second medical devices. At 1208, the coupler is attached to at least a portion of the proximal ends of both the first and second medical devices. Attaching the coupler to at least the portion of the proximal ends of both the first and second medical devices axially affixes the first and second medical devices with respect to one another. This helps to maintain the position of the first and second medical devices with respect to one another while limiting or preventing unwanted slippage of the first and second medical devices.

At 910, the first and second medical devices can be moved together. For example, the first and second medical devices can be moved together within the vasculature. The coupler, as described herein, can maintain the relative positions of the first and second medical devices, which can help to reduce or eliminate unwanted delays during the procedure.

Additionally and/or alternatively, a third medical device and/or a second coupler can be provided. The second coupler can be removable, fixed to the third medical device, or slidably attached to the third medical device, and couple the third device to one or more of the first or second medical device. The coupler (e.g., the removable coupler attached to the first medical device and/or the second medical device), the second coupler, and/or the like can be attached to the third medical device. For example, the coupler and/or the second coupler can be attached to at least a portion of a proximal end of the third medical device.

Additionally and/or alternatively, one or more (e.g., two or more, three or more, or the like) medical devices can be received by a single coupler either in a single slot or multiple slots. For example, a tapered inner delivery catheter 115, a full-length, single lumen aspiration catheter (not shown) and an outer catheter 110 having a proximal wire or rail can all be received by a single coupler (e.g., by the single slot or multiple slots) or by multiple couplers to maintain these multiple components in an axially constrained configuration, such as during advancement within the vasculature.

The removable coupler can axially fix the one or more medical devices. For example, the removable coupler can axially fix two or more medical devices (e.g., the first medical device and/or the second medical device) with respect to one another, such as outside a patient's body. The two or more medical devices can be advanced together through the patient's vasculature. During the medical procedure, the removable coupler can remain outside the patient's body. The two or more medical devices can be removed together, such as when the medical devices are fixed to one another by the coupler. Additionally and/or alternatively, the medical devices can be removed independently. For example, the removable coupler can be detached from at least one of the first or second medical devices to allow at least one of the first and second medical devices to be removed from the patient's body independently.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation, "an implementation," or the like, means that a particular feature, structure, configuration, or characteristic described is included in at least one embodiment or implementation. Thus, the appearance of the phrase "one embodiment," "an embodiment," "one implementation, "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the catheters and/or delivery systems to a specific configuration described in the various implementations.

The word "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed is:

1. An intravascular access system for facilitation of intraluminal medical procedures within a vasculature, the system comprising:

an outer catheter comprising a tubular distal portion having a lumen and a proximal extension without a lumen;

an inner catheter comprising a flexible elongate body; and at least one coupler configured to be affixed to at least a portion of the proximal extension and at least a portion of the flexible elongate body to accommodate different relative positions between the outer catheter and the inner catheter during movement of the inner catheter and the outer catheter through the vasculature, wherein the at least one coupler comprises a unitary elastic body with at least one slot configured to receive and retain the proximal extension and the flexible elongate body in a manner that axially affixes the outer catheter and the inner catheter together to allow movement of the outer catheter and the inner catheter together in the vasculature.

2. The intravascular access system of claim 1, wherein the at least one coupler further comprises a pair of wings configured to be manipulated to open the coupler.

3. The intravascular access system of claim 2, wherein the at least one coupler is V-shaped and the pair of wings are movable relative to one another to widen the at least one slot.

4. The intravascular access system of claim 2, wherein the at least one slot is positioned on a side of the coupler, and wherein the pair of wings are positioned on the side.

5. The intravascular access system of claim 2, wherein the at least one slot is positioned on a first side of the coupler, and wherein the pair of wings are positioned on a second side opposite the first side.

6. The intravascular access system of claim 2, wherein manipulation of the pair of wings towards one another is configured to cause the at least one slot to unlock, thereby allowing the proximal extension and/or the flexible elongate body to be positioned within the at least one slot or removed from the at least one slot.

7. The intravascular access system of claim 6, wherein release of the pair of wings is configured to cause the at least one slot to lock, thereby preventing movement of the proximal extension and/or the flexible elongate body relative to one another.

8. The intravascular access system of claim 2, wherein manipulation of the pair of wings in a direction away from one another is configured to cause the at least one slot to unlock, thereby allowing the proximal extension and/or the flexible elongate body to be positioned within the at least one slot or removed from the at least one slot.

9. The intravascular access system of claim 1, wherein the system includes at least two couplers.

10. The intravascular access system of claim 1, wherein the coupler and at least one of the inner catheter and the outer catheter are packaged together in a sterile package.

11. The intravascular access system of claim 1, wherein the at least one slot defines a clamp configured to contact the proximal extension and the flexible elongate body.

12. The intravascular access system of claim 1, wherein the at least one coupler is removable such that the at least one coupler is configured to be removably affixed to at least the portion of the proximal extension and at least the portion of the flexible elongate body.

13. An intravascular access system for facilitation of intraluminal medical procedures within a vasculature, the system comprising:

an outer catheter comprising a tubular distal portion having a lumen and a proximal extension;

an inner catheter comprising a flexible elongate body; and at least one coupler configured to be affixed to at least a portion of the proximal extension and at least a portion of the flexible elongate body to accommodate different relative positions between the outer catheter and the inner catheter during movement of the inner catheter and the outer catheter through the vasculature, wherein the at least one coupler comprises a unitary elastic body with at least one slot configured to receive and retain the proximal extension and the flexible elongate body in a manner that axially affixes the outer catheter and the inner catheter together to allow movement of the outer catheter and inner catheter together in the vasculature.

14. An intravascular access system for facilitation of intraluminal medical procedures within a vasculature, the system comprising:

an outer catheter comprising a tubular distal portion having a lumen and a proximal extension;

an inner catheter comprising a flexible elongate body; and at least one coupler configured to be affixed to at least a portion of the proximal extension and at least a portion of the flexible elongate body to accommodate different relative positions between the outer catheter and the inner catheter during movement of the inner catheter and the outer catheter through the vasculature, wherein the at least one coupler comprises an elastic body with at least one slot configured to receive and retain the proximal extension and the flexible elongate body, and wherein the at least one coupler comprises a pair of wings configured to be manipulated to open the coupler, wherein the at least one coupler is V-shaped and the pair of wings are movable relative to one another to wider the at least one slot, and wherein the at least one slot is located within a valley of the V-shaped coupler.

15. The intravascular access system of claim 14, wherein the at least one coupler comprises a unitary elastic body.

16. The intravascular access system of claim 14, wherein the at least one slot is configured to receive and retain the proximal extension and the flexible elongate body in a manner that axially affixes the outer catheter and the inner catheter together to allow movement of the outer catheter and inner catheter together in the vasculature.

* * * * *